United States Patent [19]

Garner et al.

[11] Patent Number: 5,776,713
[45] Date of Patent: Jul. 7, 1998

[54] MARKING OF PRODUCTS TO ESTABLISH IDENTITY AND SOURCE

[75] Inventors: Ronald Colin Garner, York, Great Britain; David J. Phillips, Charlestown, Mass.; Timothy G. Wilkinson, York, Great Britain; Frank G. Angella, Somerville, Mass.; Erwin R. Dorland; Martin W. Stow, both of York, Great Britain

[73] Assignee: Biocode Ltd., Cambridge, Mass.

[21] Appl. No.: 291,200

[22] Filed: Aug. 16, 1994

Related U.S. Application Data

[63] Continuation-in-part of Ser. No. 109,938, Aug. 20, 1993, Pat. No. 5,429,952, which is a continuation-in-part of Ser. No. 571,633, Sep. 10, 1990, abandoned, and Ser. No. 18,477, Feb. 16, 1993, abandoned, which is a continuation of Ser. No. 765,401, Sep. 24, 1991, abandoned, which is a continuation-in-part of Ser. No. 302,278, Jan. 27, 1989, abandoned.

[30] Foreign Application Priority Data

Feb. 2, 1988 [GB] United Kingdom .................... 8802237
Feb. 8, 1988 [GB] United Kingdom .................... 8802838
Feb. 8, 1989 [WO] WIPO ..................... PCT/GB89/00121

[51] Int. Cl.$^6$ ................................................. G01N 33/545
[52] U.S. Cl. ................ 435/7.92; 435/7.94; 435/7.95; 436/29; 436/543; 436/822
[58] Field of Search ....................... 436/518, 501, 436/543, 822, 29; 435/7.92, 7.94, 7.95

[56] References Cited

U.S. PATENT DOCUMENTS

| 4,441,943 | 4/1984 | Kydd ........................................ 436/56 |
| 4,770,853 | 9/1988 | Bernstein ............................... 435/295 |

FOREIGN PATENT DOCUMENTS

| 0 260 829 | 3/1988 | European Pat. Off. . |
| 0 327 163 | 8/1989 | European Pat. Off. . |
| 24 10 033 | 1/1975 | Germany . |
| GB 2 234 588 | 7/1991 | United Kingdom . |
| Ep 94927174 | 7/1997 | United Kingdom . |
| 87/06383 | 10/1987 | WIPO . |
| WO 88/09798 | 12/1988 | WIPO . |
| WO 89/07272 | 8/1989 | WIPO . |
| WO 90/14441 | 11/1990 | WIPO . |
| WO 94/04918 | 3/1994 | WIPO . |

OTHER PUBLICATIONS

Analytical Chemistry, vol. 56, No. 8, pp. 920A–9331A (1984).
Kelley, Marian M. et al., *J. Agric. Food Chem.*, vol. 33, pp. 962–965 (1985).
Newsome, William H., *J. Agric. Food Chem.*, vol. 33, pp. 528–530 (1985).
Monroe, D., *Analytical Chemistry*, vol. 56, pp. 920A–931A (1984).
Siddle, K., *Alternative Immunoassays*, (W.P. Collins, Ed.), pp. 13–37 (1985).
Translation of "Regulations For The Quartermaster Service in The Army and the Home Guard", May 15, 1975.
Kelley, Marian M. et al., *J.Agric. Food Chem.*, vol. 33, pp. 962–965 (1985).
Newsome, William H., *J.Agric. Food Chem.*, vol. 33, pp. 528–530 (1985).
Wie, Siong I. et al., *J. Agric. Food Chem.*, vol. 30, pp. 949–957 (1982).
PCT Search Report for PCT/US94/09264 published Nov. 18, 1994.

*Primary Examiner*—Mary E. Ceperley
*Attorney, Agent, or Firm*—Clark & Elbing LLP

[57] ABSTRACT

In general, the invention features a method of marking a product for identification in which a marker, composed of a low molecular weight hapten covalently bound to a compound, is associated with the product. Where the marker is non-deleterious to the product, inert with respect to the product, and not already associated with the product. The invention also features hapten markers produced by covalently binding a hapten to a functional monomer and subsequently polymerizing the hapten-labeled monomer to form a hapten-labeled polymer.

2 Claims, No Drawings

MARKING OF PRODUCTS TO ESTABLISH IDENTITY AND SOURCE

BACKGROUND OF THE INVENTION

This application is a continuation-in-part of Garner et al., U.S. Ser. No. 08/109,938, filed Aug. 20, 1993, now U.S. Pat. No. 5,429,952, which in turn is a continuation-in-part of U.S. Ser. No. 07/571,633, filed Sep. 10, 1990, abandoned, which in turn claims priority from PCT/GB89/00121, filed Feb. 8, 1989, which in turn claims priority from GB 88 02838, filed Feb. 8, 1988; as well as a continuation-in-part of Wraith et al., U.S. Ser. No. 08/018,477, filed Feb. 16, 1993, abandoned which is a continuation of U.S. Ser. No. 07/765,401, filed Sep. 24, 1991, now abandoned, which in turn is a continuation-in-part of U.S. Ser. No. 07/302,278, filed Jan. 27, 1989, abandoned, which in turn claims priority from GB 88 02237, filed Feb. 2, 1988.

This invention relates to the marking of products to establish their identity and source.

Major problems experienced in many areas of the world and in connection with many different products is that of product counterfeiting, unauthorized distribution and sale of a product (e.g. grey market trading, parallel trading, product diversion), as well as false liability based on product substitution.

Throughout the world, traders provide the products they sell with a visually distinctive appearance, packaging or labels so that customers can distinguish their products from those of others. As a result, their customers learn to associate the visually distinctive appearance with certain standards of quality, and, if they are satisfied with those standards, will buy products provided with that visually distinctive appearance in preference to others. Once customers have acquired a preference for products provided with a particular visually distinctive appearance, the traders become vulnerable to product counterfeiting.

A counterfeit product consists of a product that is provided with a visually distinctive appearance confusingly similar to that of a genuine product. Customers seeing the visually distinctive appearance provided to the counterfeit product buy this product in the expectation that they are buying a genuine product.

There are many ways known of providing products with a visually distinctive appearance. In general, the visually distinctive appearance is provided either directly to the product or to an article with which the material is associated, for example a label, wrapper or container. The visually distinctive appearance may be, for example, a distinctive shape or configuration, a distinctive marking, or a combination of the two. A particularly preferred visually distinctive appearance is a trademark.

The material of a counterfeit product may be the same as, or different from the material of a genuine product. Often the material of the counterfeit product is the same, but of inferior quality. For instance, it is usually difficult to distinguish a chemical product having a particular chemical formula and made by one manufacturer, from the same chemical, with the same formula, but made by a different manufacturer. This is particularly so if the two manufacturers use the same production process. For this reason, it is not difficult for the unscrupulous to establish the chemical formula of an active ingredient in a composition, and the relative amounts of the various ingredients in the composition, and then pass off his own product as that of another manufacturer.

In addition to product counterfeiting, product adulteration is another major problem. Product adulteration takes place when a product is tampered with such as by dilution. An example of such a problem lies in the adulteration of lubricating oils, or other oil based products, by addition of a counterfeiter's oil to a genuine product. Such adulteration is not only financially damaging to the oil manufacturer but the consequent lowering of performance which can occur can cause damage to the consumer and consequently harm the reputation of the genuine product.

A method of overcoming this problem has been previously proposed involving the incorporation of dye in the product. Such a strategy is easily copied.

WO 87/06383 discloses a method of labelling an item or substrate by means of macromolecules, in particular, DNA or proteins.

European patent application publication number EP-A-0260829 discloses monoclonal and polyclonal antibodies which may be used to identify chlorinated phenols, particularly pentachlorophenol, in materials and to determine the concentration of the chemical in those materials. It is noted in the introduction to the specification that pentachlorophenol is added to materials as a pesticide or a preservative. EP-A-0260829 does not disclose the identification of chlorinated phenols in products or the use of chlorinated phenols as marker compounds.

In a poster presentation given by M. J. Wraith et al., at the 6th International Congress of Pesticide Chemistry, Aug. 10–15th, 1986 in Ottawa, Canada, entitled "Development of Immunoassay Methods for Pyrethroid Insecticides", there were disclosed protein conjugates of m-phenoxybenzoic acid and dichlorovinyl cyclopropane carboxylic acid, and polyclonal antibodies prepared using these protein conjugates. Also disclosed was the analysis of the cypermethrin metabolites, m-phenoxybenzoic acid and dichlorovinyl cyclopropane carboxylic acid in black tea, water and soil. No disclosure was made of the use of either m-phenoxybenzoic acid or dichlorovinyl cyclopropane carboxylic acid as a marker compound, nor of the detection by immunoassay of either compound in any material provided with a visually distinctive appearance.

SUMMARY OF THE INVENTION

In general, the invention features a method of marking a product for identification in which a marker, composed of a hapten or composed of a hapten covalently bound to another chemical compound, preferably a polymeric compound, is associated with the product. The marker is non-deleterious to the product and not already associated with the product. Thus, the presence of the marker can only be easily established by someone who knows the identity of the marker, but can not be routinely determined by a counterfeiter or other person unfamiliar with the marker. Thus, a counterfeit and a genuine product can be distinguished by the absence of the marker in the former and the presence of the marker in the latter.

The product is generally a commercial product and may be either solid, liquid, semisolid, or gas. The marker may be added directly to the product (e.g., attached to a surface of the product or mixed with the product itself) or associated with a label, tag or other product packaging material.

One type of preferred marker of the invention is composed of a hapten covalently bound to a polymeric compound, where the marker is produced by first covalently binding a hapten to a functional monomer, and then polymerizing the hapten-monomer compound to form a polymer having covalently-bound hapten. The molar ratio of hapten to polymer present in markers made by this method may be easily varied by varying the relative amounts of hapten-labeled monomer and unlabeled monomer in the polymerization mix. Preferred functional monomers include substituted styrene and the family of acrylic monomer.

The invention also features kits for detecting a hapten marker(s) in a marked product. One version of a detection kit includes a sample-receiving solid support which has the hapten to be detected bound to its surface, a container containing a specific binding member specific for the hapten, and detecting means for detecting formation of specific binding member-hapten complexes. Preferably, the specific binding member is an anti-hapten antibody. Preferably, the detecting means is a detectably labeled antibody which specifically binds the anti-hapten antibody. Preferred detectable labels include enzymes, chemiluminescors (e.g. luciferin), and chromophores (e.g. dyes, colored latex beads, dyed particles, pigments, metal sol particles (e.g. gold or silver metal sol particles), dye encapsulated liposomes, carbon). Alternatively, the detection kit includes a sample receiving solid support having a first specific binding member specific for the marker bound to its surface and a container containing a detectably labeled second antibody which is specific for the hapten marker.

Another class of markers of the invention is composed of a hapten marker, which may be composed of a hapten or may be composed of a hapten covalently bound to a chemical compound, having a detectable physical characteristic, e.g. color. The physical characteristic of the hapten marker is not detectable at hapten marker concentrations present in the marked product, but is detectable upon concentration of the hapten marker. The marker is thus detected by concentrating the hapten marker from a sample of the marked product to provide the hapten marker at a concentration which allows detection of the concentration-dependent, physical characteristic of the hapten marker. The physical characteristic of the hapten marker may be associated with the hapten portion of the marker or the non-hapten portion of the marker. In preferred embodiments, the marker is concentrated from the sample by immunoconcentration through either immunoprecipitation or use of an immunoaffinity column, using an anti-hapten antibody which specifically binds the hapten.

The invention also features a kit for detecting hapten markers having a detectable, concentration-dependent, physical characteristic. The kit includes a sample receiving solid support which has an anti-hapten antibody bound on it surface.

By "marker" is meant a compound composed of a hapten and/or a hapten covalently bound to a chemical compound, preferably a polymeric compound.

By "hapten" is meant a low molecular weight molecule which does not elicit a significant antibody response when used as an immunogen alone. When the hapten is coupled (i.e. covalently bonded) to a larger, carrier molecule (e.g. keyhole limpet hemocyanin, bovine serum albumin, chicken gamma globulin), and the hapten-carrier compound used as an immunogen, hapten-specific antibodies are produced. Generally, haptens have molecular weights under 1,000, and thus exclude proteins, DNA molecules, and other antigens.

By "polymeric compound" is meant a compound, normally a large, high molecular weight compound, composed of monomeric units which are different from the hapten. As used herein, "polymeric compound" is meant to encompass polymers, copolymers, and complex copolymers. Exemplary polymeric compounds include proteins, peptides, oligonucleotides, polystyrene, and various synthetic polymers well known in the art.

By "functional monomer" is meant a monomeric unit capable of polymerizing to form a polymeric compound. As used herein, functional monomers are capable of both covalently binding a hapten and subsequently polymerizing to form a polymeric compound.

By "hapten-specific antibody" is meant an antibody which substantially specifically binds a hapten molecule. Hapten-specific antibodies may be either polyclonal or monoclonal antibodies.

By "marking a product for identification" is meant associating a marker with a product so that the source, identity, or other information about the product including production date, batch, and shelf-life may be established. Identification of a marked product can also facilitate: 1) monitoring of manufacturing or other processes, including monitoring process streams and blending controls; 2) product monitoring for security or regulatory purposes, such as marking the source country of products for customs and marking regulated substances; 3) detecting and monitoring spillages of marked materials, including the detection of residues of marked products, such as pesticides, herbicides, fertilizers, toxic wastes, organic pollutants (such as TBT and dioxins) and other chemicals; 4) tracing a product, such as marking a process chemical to monitor the rate of addition of the chemical to a system (e.g. a water system) in order to optimize chemical dosage; and 5) studies of biodegradation of a compound, e.g. in soil biodegradation studies. Marking a product for identification also includes the associating a product with a particular concentration of a marker, so to facilitate the detection of product aldulteration by way of dilution, concentration changes, or the addition of foreign substances.

By "physical characteristic of a hapten marker" is meant a characteristic inherently associated with a hapten marker, such as color, density, weight, and optical activity.

By "concentration-dependent physical characteristic" is meant a physical characteristic which is only detectable at a particular concentration of a compound. As used herein, "concentration-dependent physical characteristic" particularly refers to a physical characteristic of a hapten marker which is not detectable at the hapten marker concentration employed in a marked product, but which is detectable upon concentration of the hapten marker, e.g. by extraction and precipitation of the hapten marker from the marked product, to a concentration greater than the hapten marker concentration in the marked product.

By "specific binding member" is meant a molecule capable of specifically binding to a marker. The specific binding member may bind the marker by either binding to the hapten portion of the marker or by binding to a chemical compound or polymeric compound (i.e. the non-hapten portion of the marker) to which the hapten is covalently bound. Specific binding pairs are, e.g., antibodies and haptens; biotin and avidin and ligands and receptors.

The present invention allows the practitioner to, for the purposes of marking a product, develop or select the minimum chemical structure (i.e., hapten) which will be specifically recognized at low concentrations by a developed or selected specific binding member (e.g., antibody) and to chemically attach this minimum recognizable structure to a custom selected compound to create a marker which provides the required characteristics for a particular product marking application. Such required marker characteristics may include: (1) solubility or non-solubility in a product or solvent in which the hapten alone is or is not soluble; such solubility or non-solubility can be important either for efficiently incorporating the marker into the product, or for extracting the marker for testing; (2) stability during extremes of temperature, pH or other physical or chemical conditions inherent in many manufacturing processes, which would otherwise destroy the hapten or hapten binding site; (3) stability within a product or adherence to the surface of a product during conditions of use or storage under which the hapten alone or binding site alone would not be stable, would not adhere or would not retain the spatial orientation required for effective recognition.

Furthermore, the tagging of a compound with the minimum chemical structure which allows for recognition by a specific binding member and the use of this tagged compound in a fixed ratio to untagged compound allows for tracing of the tagged compound during a process, in the final product, or upon release or after release in the environment, in a manner which will closely model the behavior of the untagged compound.

The flexibility of binding partner selection which is independent of compound selection also allows more than one compound, or in fact a large group of different compounds, to be made recognizable by attachment of the same specific binding member to each. Such a capability significantly broadens the number of unique markers which can be employed in product marking and significantly reduces the number of unique test reagents (binding pairs) which must be developed and manufactured in order to identify this broad range of markers in use. In one embodiment, a range of compounds each with a unique but related concentration dependent physical characteristic (e.g., color) can each be used as a unique marker but can be concentrated and detected with the same test.

In one embodiment of the invention, the attachment of a hapten allows the practitioner to make recognizable by a specific binding member a compound for which one skilled in the art could not develop a specific binding member (e.g. a compound that when injected into an animal, either independently or when linked to common immunogen carriers known in the art, will not elicit an immune response specific to the compound). This allows compounds that otherwise could not be used as markers to be effectively used as markers, or can allow compounds which cannot presently be assayed by a specific binding pair assay to be assayed by such methods.

A specific binding pair assay, such as immunoassay, can be employed to test a product for a marker in a remote location by relatively inexperienced personnel. Immunoassays and related techniques, such as immunoaffinity concentration coupled to physiochemicals methods of analysis (e.g. HPLC and fluorimetry), allow for the use of accurate reference procedures in the laboratory. This combined ability to test in both the field and the laboratory allows products to be screened for a marker on location and/or sent to a secure laboratory for testing, depending on which mode of testing is most appropriate for the application.

Other features and advantages of the invention will be apparent from the following description of the preferred embodiments thereof, and from the claims.

DETAILED DESCRIPTION

Markers

The marker of the invention is capable of being detected by immunoassay and/or by concentration of the marker and detection of a concentration-dependent physical characteristic. The marker should be compatible, i.e., non-deleterious, with the product which it marks. The marker may be composed of a hapten or a hapten covalently bonded to a polymeric compound. Preferably the marker will be non-toxic if used in a manner in which the it is intended to be ingested. Preferably the marker is visually undetectable when present in the product.

The marker hapten should in general be one which is not normally present in the chemical or composition; for example, it is not a by-product of the production process, normal impurity, or standard additive for that chemical, or chemical composition. In preferred embodiments, the marker compound is present in very low concentrations, e.g., in the order of parts per million or parts per billion. Although the marker is preferably inert With respect to the product in the sense that it does not react with the product which it labels, it must nevertheless be capable of binding to a specific binding member, e.g. an antibody, preferably a monoclonal antibody. Moreover, the ability to detect the marker should not be adversely affected by interaction with the product or compound it labels. For example, where the marker is to be detected by immunoassay, the marker is still capable of binding to a marker-specific antibody.

Depending on the specific application, certain criteria must be considered in selecting an appropriate chemical compound which is capable of performing acceptably as a marker. Most importantly, the compound must possess a specific molecular moiety, which is recognizable to a specific binding member (e.g., a specific antibody). Exemplary hapten marker compounds may typically include bulky, substituted aromatic compounds, such as 4-amino-1-naphthalenesulfonic acid:

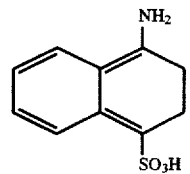

Other haptens suitable for use as a marker compound have been found to be m-phenoxybenzoic acid and mordant yellow 7. Other preferred compounds for marking are 4-aminonaphthalene-1-sulphonic acid, amaranth, dafcol brown, 4-amino-1, 1-azobenzene-3, 4'-disulphonic acid, 4-hydroxy-3-methoxycinnamic acid, 4-hydroxy-3-methoxyphenyl-3-buten-2-one vanillin, ethyl-4-hydroxy-3-methoxycinnamic acid, Chromotrope FB, Ponceau 4R, ponceau S, tropeolin O, curcumin, coniferyl alcohol, hexyl vanillate, acetovanillone. A list of these marker compounds is set forth below in Table 1.

TABLE 1

| MARKER CHEMICALS TO WHICH ANTIBODIES HAVE BEEN GENERATED | |
|---|---|
| M-phenoxybenzoic acid | Chromotrope FB |
| 4-Aminonaphthalene-1-sulphonic acid | Ponceau 4R |
| Amaranth | Ponceau S |
| Dafcol Brown | 4'-disulphonic acid |
| 4-Amino-1, 1-azobenzene-3, 4'-disulphonic acid | Tropeolin O |
| Mordant yellow 7 | Curcumin |
| 4-Hydroxy-3-methoxycinnamic acid | Coniferyl alcohol |
| 4-Hydroxy-3-methoxyphenyl-3-buten-2-one | Hexyl vanillate |
| Vanillin | Acetovanillone |
| Ethyl 4-hydroxy-3-methoxycinnamic acid | |

It will be appreciated that a wide range of compounds are suitable as hapten marker compounds so long as they are compatible with and non-deleterious to the product being marked. Thus the use of oil-compatible, water-compatible and solids-compatible or food grade compounds as marker compounds is envisaged dependent on the product being marked.

The use of optically active marker compounds may be particularly advantageous, as it is difficult to distinguish between optically active forms of compounds by conventional analytical techniques, particularly when only trace quantities of the compound are available for analysis. Antibodies which are selective for a particular optically active form of a compound can be produced to facilitate detection of such optically active marker compounds in a product.

In a preferred embodiment of the invention, the marker has a detectable physical characteristic. Detectable physical characteristics of a marker include, for example, color, weight, density, magnetic attraction, luminescence, fluorescence, absorbance, chemical reactivity, or various characteristics which can be detected by optical methods well known in the art. Preferably the physical characteristic of the marker is color or fluorescence. The physical characteristic may be conferred upon a hapten marker by a physical characteristic of the hapten used as (or in) the marker, and/or by a physical characteristic of a chemical compound or polymeric compound which is covalently bound to a hapten.

Preferably, detection of the physical characteristic of the hapten marker is not possible at the low concentrations of hapten present in a marked product. Upon concentration of the hapten marker from a product sample (e.g. by immunoprecipitation or immunoconcentration) to a concentration that is greater than the hapten marker concentration in the marked product, the physical characteristic is readily detectable by, for example, detection of a particular color of the concentrated test sample. Preferably, the hapten marker may be detected by its physical characteristic following at least a 2-fold increase, preferably at least about a 5-fold increase, more preferably at least about a 10 to 10,000 fold increase in hapten marker concentration relative to the concentration of the hapten in the marked product. Exemplary haptens which may be detected by a concentration-dependent physical characteristic include 4-amino-1,1-azobenzene-3,4-disulphonic acid, Chromotrope FB, and Ponceau 4R.

In a preferred embodiment of the invention, the marker compound is composed of a hapten which is covalently bound to a pre-existing or pre-formed polymeric compound. The polymeric compound is normally a large, high molecular weight compound, composed of monomeric units. The polymeric compound may be composed of a single type of monomeric unit (i.e. homogeneous with respect to monomeric composition), or may be composed of 2 or more different types of monomeric units (e.g. a copolymer or complex copolymer). Exemplary polymeric compounds include peptides, proteins, protein fragments, oligonucleotides, and synthetic polymers, particularly organic synthetic polymers such as styrene, phenolic resins, polyallylamines, acrylates, and modified polyvinylchloride. The polymeric compound selected must be capable of covalently binding a selected hapten and must be non-deleterious and inert with respect to the product to be marked. Moreover, the polymeric compound must not substantially affect the ability of the hapten to be detected, e.g. to bind to a hapten-specific antibody or to provide a concentration-dependent, detectable physical characteristic. Preferably, covalently binding the hapten marker to a polymeric compound provides for enhanced stability and immunodetectability of the hapten marker.

In a further embodiment of the invention, the hapten marker is composed of a hapten which is covalently bound to a chemical compound. Exemplary chemicals which may be labeled with a hapten marker include agrichemicals such as sulphonyl urea herbicides; industrial chemicals such as biocides, dyes and fluorescent tracers; pharmaceuticals; surfactants; adhesives and resins such as wood resins, isocyanate glues and epoxy resins; ink binders such as phenolic resins and epoxy resins; food additives such as bulking agents, vitamins and flavorants; and process chemicals (e.g. chemicals used in water systems) such as biocides, flocculating polymers, corrosion inhibitors, and anti-scalants. Preferably, the covalently-bound hapten does not substantially adversely affect desirable characteristics of the chemical compound, such as chemical activity, non-toxicity (e.g. where the compound is a food additive), and sensitivity to degradation.

Methods for chemically coupling haptens to polymeric compounds or chemical compounds such as those exemplified above are well known in the art. The compounds may be labeled with one or multiple hapten molecules or may be labeled with a single type or multiple types of haptens, thus providing a marker composed of a combination of hapten labels. Thus, multiple different haptens, each of which may be recognized by distinct specific binding members (e.g. antibodies specific for a particular hapten) can be covalently bound to the polymeric compounds or chemical compounds. Alternatively, separate molecules of the polymeric compound or chemical compound, which are otherwise identical, may be labeled with different haptens. Thus, the haptens and hapten markers may be used in numerous combinations in the marking of a product.

Alternatively, the hapten-polymer marker may be produced by first covalently binding a hapten to a functional monomer to provide a hapten-labeled monomer. The hapten to be covalently bound to a functional monomer must contain a molecular moiety, or functional group, which is capable of reacting with and covalently bonding to a functional monomer to produce a hapten-labeled monomer. Exemplary reactive groups include amino, carboxylic acid, sulfonic acid, acid chloride, hydroxyl, oxirane, hydroxyl, chlorine, or ester groups. Methods for covalently binding a hapten to a functional monomer are well known in the art. The labeled monomer is then polymerized to form a hapten-labeled polymer.

Preferably, the covalently-bound hapten does not substantially adversely affect that ability of the monomer to polymerize. More preferably, the hapten-labeled monomer is capable of forming a polymer by polymerization with both unlabeled monomers and hapten-labeled monomers. Selection of a functional monomer to react with a particular hapten require at least two functionalities: 1) a double bond capable of undergoing free radical, addition polymerization, or difunctionality capable of undergoing condensation polymerization; and 2) a reactive site capable of reacting with and covalently bonding to the hapten. In the general case of unsaturated monomers, exemplary functional monomers include functional monomers based on substituted styrene and functional acrylic monomers, such as (meth)acrylic esters. Exemplary substituted styrene and (meth)acrylic esters are exemplified below:

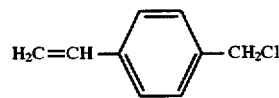

-continued

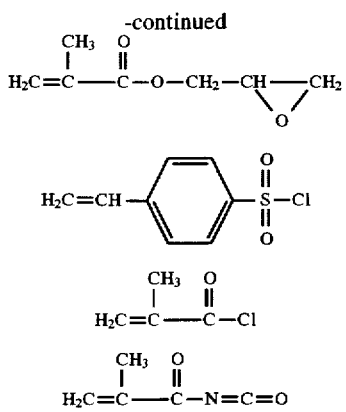

Thus, the functional monomers which may be used to produce hapten-polymer markers are those monomers which are capable of covalently binding a hapten and retaining the ability to polymerize to form a hapten-labeled polymer. Exemplary functional monomers include amino acids, nucleotides, styrene having a hapten-reactive functionality, ethylene oxide, epichlorohydrin and propylene oxide.

Synthesis of hapten-labeled polymers by polymerization of hapten-labeled monomers provides for enhanced control of polymer labelling and can also facilitate increased loading of the hapten onto the polymer. For example, by varying the relative concentrations of unlabeled and hapten-labeled monomers present during polymerization, a polymer having varying amounts of hapten may be produced. The resultant hapten-polymer marker may be composed of a molar ratio of hapten to polymer of from between about 1:1 to 10:1, preferably from about 2:1 to 100:1, more preferably from about 10:1 to 1,000:1, depending upon the desired hapten concentration in the product. Furthermore, monomers labeled with different haptens may be polymerized to provide a hapten-polymer marker composed of multiple kinds of hapten labels.

The hapten polymer conjugates can be used not only to label surfaces, but can be incorporated into products (either liquids or solids) as well. Moreover, the hapten bound to the functional monomer may be used to detect either the monomer alone or the presence of the hapten-labeled functional monomer in a polymer.

The hapten-labeled functional monomers, chemical compounds, or polymeric compounds may also have an additional chemical moiety or group which can be: 1) a second hapten, to facilitate detection of the hapten marker and/or increase the sensitivity of the detection assay, particularly where the detection assay is a sandwich binding assay; 2) a signal compound, which can be detected to allow for enhanced test sensitivity (e.g. an antibody on a solid support can be used to bind the hapten and concentrate the monomer or compound, and the signal compound bound to the monomer or compound detected to assay for the presence of bound hapten marker); and/or 3) a functional chemical moiety to allow for binding or concentration on a solid support by non-immunological (e.g. antibody-based) means. The functional chemical moiety may, for example, provide for an ionic charge of the overall hapten marker molecule, so that the hapten marker may be bound to the support through an ionic interaction. Alternatively, the functional chemical moiety may react with a compound coated on a solid surface so as to covalently bind the hapten marker to the support.

As an extension of the ability to use small organic molecules for the purpose of identifying and distinguishing between batches of high added value products, it is possible to conjugate numbers of different polymeric compounds (e.g. amino acids) to a given hapten to which antibodies have been made. While this does not alter the detection of the hapten (e.g. binding of the hapten of the marker to an immunoaffinity column), it renders it more easily separable by a detection method such as HPLC or by binding to an antibody specific for the polymeric compound (e.g. amino acid sequence) conjugated to the hapten. Indeed, by HPLC or immunoprecipitation, different amino acid(s) and/or different sequences of the same amino acids could be easily separated. The number of possible combinations is very large as there are 20 natural amino acids and many synthetic chemicals which can be used in such a process. Selection of conjugates depends on their solubility in the solvents used during binding of anti-hapten or anti-peptide conjugate antibodies to the hapten marker.

Products for marking It will be appreciated that the marker compound may be associated with the product in a wide variety of ways. Thus the marker compound may be present in or on all or part of the product, or in or on all or part of a label, wrapper, container or other packaging material associated with the product. The marker compound is usually mixed with the product, but may alteratively be present independently of the product, for example the marker may be present in the product packaging or labelling.

The product marked may be solid, semi-solid, fluid, or gas.

Examples of solid products include polymers, plastics, and rubbers; pharmaceutical tablets, capsules and powders; solid formulations of agrochemicals such as insecticides, herbicides, fungicides and fertilizers; textiles such as clothing; designer or specialty products such as crystal, china, and silver goods; original works of art such as paintings and sculptures, recordings such as gramophone records, tape cassettes, floppy discs and compact discs; electrical goods such as television sets, computers and radios; motor vehicle components and cameras; paper such as documents, confidential papers, notes, securities, labels, and packaging; chemical products such as biocides, cosmetics such as creams; and food products.

Examples of fluid products include oil-based products such as lubricating oils, gasoline, diesel and liquified petroleum products; paints and coatings; perfumes; cosmetics; inks; drinks such as wine, whisky, sherry, gin and vodka; liquid pharmaceutical formulations such as syrups, emulsions and suspensions; liquid agrochemical formulations; chemical compositions; and industrial solvents. The fluid product is preferably liquid. One preferred class of products encompasses oil based products such as lubricating oils.

Examples of gases include stack emissions (e.g. for pollution tracing), air parcels (e.g. for study of weather patterns), and air samples within storage containers (e.g. to ensure that such containers have not been opened).

When the product is an oil-based product such as a lubricating oil, the compound used as a marker compound preferably has a log P in the range of from −2.5 to +5.0, preferably from −1.5 to 4.5, most preferably from 0 to 4.0. (Log P as used herein means the logarithm of the partition coefficient of a compound between octanol and water at 25° C.). Thus, m-phenoxybenzoic acid, for example, has a log P of 3.9.

When the product is a liquid, the marker compound is preferably colorless at concentrations present in the marked product and soluble in the liquid product so that its presence can only be detected by subsequent assay. It is preferably also odorless at marker concentrations present in the marked product.

Preferably only trace quantities of marker are used. Typically a marker compound will be incorporated with a product at a concentration in the range of from 1 part per billion (ppb) to 25 parts per million (ppm). Preferably the concentration will be in the range of from 20 ppb–500 ppb. Where the hapten marker is to be assayed through direct detection of the hapten marker on the surface of the product (e.g. in an ink or coating placed on the product surface), the percent incorporation of the hapten marker into the polymer will generally be in the range of about 0.1% to 5% by weight.

The ability to detect concentrations of marker compound at very low concentrations, i.e., in the parts per billion range, is a particular advantage of the method according to the invention. Thus only small quantities of marker compound need to be used.

According to another aspect, the invention provides an oil-based product comprising from 1 ppb to 25 ppm of a visually undetectable, substantially water-soluble marker compound having a log P in the range of from −2.5 to 5.0.

Preferably several markers are included in a chemical or chemical composition products. The ratios of the concentrations of the markers in each chemical or composition labelled are then preferably unit ratios, e.g. in the case where there are two markers the ratio of concentration of one to that of the other may be 1:1, 1:2, 1:3, 1:4, etc. The total amount of marker compound(s) added is such that each marker compound is preferably added at a level of not more than 10 parts per million, and more preferably at not more than 100 parts per billion (by weight).

In one embodiment, a plurality of markers are present these possess a common site which enables them to bind to, and be concentrated on the same specific binding member, while they remain separable by subsequent analytical techniques. Thus in some embodiments at least one of the hapten marker compounds is covalently bound to an amino acid, nucleic acid, oligonucleotide or oligopeptide substituent which does not affect the binding of the marker compound to its specific binding member. Such substituents make marker compounds more easily distinguishable from each other by analytical techniques such a HPLC. For example, the 4-amino-1,1-azobenzene-3,4-disulphonic acid antigen may be coupled to oligopeptides of varying lengths and the [4-amino-1,1-azobenzene-3,4-disulphonic acid]-oligopeptides used as markers. The markers can subsequently be extracted from the marked product by immunoprecipitation with an anti-[4-amino-1,1-azobenzene-3,4-disulphonic acid] antibody. The immunoprecipitated markers may then be further analyzed by size separation on an SDS-PAGE gel or by HPLC.

In one application of the invention, a hapten marker is applied to a surface using an impact or non-impact printing method. The laid down hapten can be subsequently visualized by the application of the other member of the specific binding pair. Since haptens are either not compatible with the ink formulation or do not have good adhesion properties to the surface, it is preferable to provide the marker as a covalently bound hapten-polymeric compound, where the hapten is covalently bound to a polymeric backbone. The hapten-polymer is soluble in the ink formulation and can still be detected (e.g. recognized by the specific binding pair member) after application. Preferably, the hapten-polymer marker adheres well to surfaces such as glass, plastic, metal, coated packaging, pressure sensitive labels, holograms and polyester.

Alternatively, the hapten marker can be incorporated into coatings which are then applied to the surface of a product to be marked. Exemplary coatings include paints, varnishes, plastic or rubber-based coatings, as well as other coatings well known in the art. These coatings can be applied to credit cards, pressure sensitive labels, security labels, holograms, product packaging, or other visual mark of authenticity (e.g. a trademark or logo). The hapten marker-labeled coatings can be applied directly to the surface of products (e.g. electronic equipment, appliances, photographs, glass, metal, and plastic). Detection of the hapten marker in the coating may be performed by assaying a sample of the product coating. Alternatively, the hapten marker in the coating may be detected by directly assaying the surface of the marked product in a reversible, non-destructive manner through reaction with a detectably labeled specific binding member specific for the hapten marker in the coating. Once the hapten marker is visualized on the surface of the product, the specific binding member may be dissociated from the hapten marker by various methods well known in the art including organic solvents, high ionic salt buffers, and alteration of pH. Preferably, the dissociation will be performed by a method which preserves the hapten marker intact to allow for future visualizations.

In one embodiment of the method, the hapten is chemically linked to a polymer through suitable conjugation chemistry. The subsequent hapten-reacted polymer is dissolved or suspended in an ink formulation capable of being applied through ink jet printing or other printing methods known in the art. Once dry, the hapten-polymer can be revealed by application of the specific binding pair linked to a signal compound such as an enzyme, latex bead or fluorescent tag.

Marker detection

The marker haptens may be detected in a sample of the product either qualitatively or quantitatively. Quantitation of the hapten marker in a product facilitates detection of product alduteration by dilution of the original product.

Quantitation of the hapten marker can also be used in assessing the physical parameters of fluid systems. For example, one can mark a known volume of a liquid (e.g. water) at a known concentration, add this marked sample to a fluid system of unknown volume, disperse the marked sample in the fluid system, assay a sample from the fluid system, and calculate the dilution effect to determine the volume of the fluid system.

The marker compound can be incorporated with the product in an aqueous medium, and an assay to detect the marker may be carried out directly on a sample thereof. The sample may be filtered to remove solids, if necessary. Otherwise the marker compound may be brought into aqueous solution.

In general, producing a sample of a product to assay for a marker compound in aqueous solution will comprise one or more steps selected from solvent extraction of the marker compound from the product; dilution of the product with an aqueous solvent; filtration; evaporation; precipitation; and solid phase extraction of the marker compound, e.g. purification of the marker compound using an ion exchange resin, chromatography (e.g. using silica), or immunoaffinity chromatography. In the case of a marked oil-based product solvent extraction appears to be necessary.

The solvent chosen for extracting the marker compound from the product prior to assay naturally depends on the natures of the product and the marker. Depending upon the natures of the product and the marker, the solvent will in general comprise one or more of water; hydrocarbons, for example benzene, toluene, xylene, hexane, heptane and octane; sulphoxides, for example dimethylsulphoxide; halogenated hydrocarbons; chlorinated solvents, for example chlorobenzene, methylene chloride, chloroform and carbon tetrachloride; ethers, for example diethyl ether, dioxane and tetrahydrofuran; amides, for example dimethylformamide and dimethylacetamide; nitriles, for example acetonitrile; alcohols, for example methanol, ethanol and propanol; esters, for example ethyl acetate; and ketones, for example acetone. Preferably the solvent comprises water and/or a water miscible organic solvent. For example, when testing lubricating oils marked with m-phenoxybenzoic acid, a suitable extracting solvent is a mixture of a diluent for the oil such as hexane, a water-miscible organic solvent such as acetonitrile, and water. Optionally the extraction solvent may also comprise buffer salts such as Tris buffer (Tris [hydroxymethyl]amino-methane). The solvent system used preferably yields the extracted marker compound in an aqueous phase suitable directly for the subsequent detection assay.

The present invention facilitates the identification of several different batches of a product (e.g. a chemical or chemical composition) by the use of a single marker compound. This is because a single marker compound may be employed in different concentrations in different batches and each batch identified by determination of the concentration of the marker in that batch.

In certain preferred embodiments a plurality of marker haptens are included in a chemical or composition. In this case the number of possible permutations of concentration and markers is increased and batches may be identified with increased certainty by measuring relative concentrations of the markers.

In some embodiments of the present invention the marker hapten is extracted from the product into a solvent before detection. Where the detection method uses a specific binding member (e.g. a hapten-specific antibody), the solvent is preferably one which is compatible with the specific binding member. Alternatively, where the extraction solvent is incompatible with the specific binding member the extract may be diluted with a compatible solvent before binding to the specific binding member.

Specific binding members are molecules which substantially specifically bind to the hapten marker to be detected in a sample of a marked product. Exemplary specific binding member-hapten marker pairs include antibody-antigen pairs, receptor-ligand pairs (e.g. hormone receptor-hormone pair), carbohydrate-lectin pairs, avidin-streptavidin pair, or other molecules which are capable of interacting through specific, intramolecular interactions such that the binding of the first molecule of the pair to the second molecule of the pair is substantially specific. The specific binding member is preferably an antibody or fragment thereof which retains antigen-specific binding (e.g. Fab), and particularly preferably a monoclonal antibody. The specific binding member or members are desirably bound on a solid support, such as an immunoaffinity column.

In a preferred embodiment, assay of the marker hapten by contact with an antibody is accomplished by competitive enzyme-linked immunosorbent assay (ELISA), although other immunoassay methods may be employed, including enzyme-mediated immunoassay, sandwich immunometric assays, immunoassays using lateral flow devices, and other immunoassays well known in the art.

Numerous variations on each of these immunoassay methods are well known in the art. For example, the sandwich assay may be performed in at least three different manners. First, the sample receiving support may have a surface-bound antibody which specifically binds a non-hapten portion of the marker (e.g. the polymer, monomer or chemical compound covalently bound to the hapten) to capture the marker on the support. Binding of the hapten marker is then detected by the binding of a second, detectably-labeled antibody which specifically binds to the hapten portion of the hapten marker.

Alternatively, the hapten marker may be bound to the support through non-specific interactions between the hapten marker and the support surface or a coating on the support surface. For example, the hapten marker may be bound to the support through an ionic interaction between the hapten marker and the support (e.g. binding of BSA to polystyrene in a microtiter plate well). Methods for increasing such non-specific interactions are well known in the art (e.g. coating the support surface with a charged molecule to increase ionic interaction with the hapten marker).

In another variation of the immunoassay, the support-bound antibody may be specific for the hapten of the hapten marker and the second, detectably labeled antibody may also bind the hapten, specific for either the same hapten epitope or different hapten epitope. A further variation on the detection assay uses a sample receiving support having a surface-bound, first antibody which binds one of two or more haptens present in the marker. Binding of the marker to the first antibody is detected by the binding of a detectably-labeled second antibody which recognizes a second, different hapten present in the marker.

Actual detection of the result of the assay may be by colorimetric means or by alternative detection means such as chemiluminescence or fluorescence. Where the marked product contains multiple hapten markers, the presence of the markers may be detected simultaneously by using differentially labeled antibodies which are specific for each particular type of hapten.

In a further embodiment of the invention, the hapten marker has a detectable, concentration-dependent physical characteristic, such as color or fluorescence. While the hapten marker is preferably not detectable in the product, the physical characteristic of the hapten marker becomes readily detectable upon concentration of the marker to a concentration greater than the hapten marker concentration in the product (i.e. detection of the physical characteristic is concentration-dependent). Thus, detection of such hapten markers is accomplished by concentrating the hapten marker from the product by, for example, precipitation, immunoprecipitation or other methods known in the art. Generally, the hapten marker may be detected by its physical characteristic following at least a 2-fold increase, preferably at least about a 5-fold increase, more preferably at least about a 10 to 10,000 fold increase in hapten marker concentration relative to the concentration of the hapten in the marked product. Where the detectable, concentration-dependent physical characteristic is color, the presence of the hapten marker may be detected by direct observation or by use of a spectrophotometer.

Preferably, the hapten marker is concentrated by contacting a sample of a product with an specific binding member, preferably an antibody, specific for the hapten marker. The anti-marker antibody may be in solution or may be bound to a solid support. The product sample is incubated with the anti-marker antibody for a time sufficient for formation of immune complexes of hapten marker and antibody. Where the antibody is in solution, the immune complexes are concentrated (e.g. precipitated). Upon binding of the hapten marker to the support-bound antibody, or upon concentration of the antibody-marker immune complexes, the physical characteristic of the hapten marker becomes readily apparent.

It will be appreciated that such detection methods are well suited to field operation, as no complex laboratory equipment is required.

Production of hapten-specific antibodies for marker detection

The hapten markers are molecules to which antibodies may be generated by administering them in association with a carrier molecule.

Such antibodies are raised by known techniques which allow one to obtain monoclonal or polyclonal antibodies specific to a particular hapten.

Antibodies are proteins produced in animals by antibody-producing cells known as B-lymphocytes in response to the exposure of the animal to foreign compounds (antigens). These antibodies bind specifically to the particular compound which stimulate their production.

Antibody-producing cells arise in the spleen of an animal when the animal has been immunized with an immunogenic compound. Not all compounds are immunogenic. In general, compounds with a molecular weight of below 2,000 are not immunogenic. However, antibodies which are specific for such compounds (known as haptens) may be obtained by chemically binding the hapten to a larger immunogenic carrier such as a carbohydrate or protein, and immunizing an animal with the resultant immunogenic conjugate.

The attachment of hapten to immunogenic carrier may be achieved using a bifunctional molecule in a two-stage chemical reaction. This provides a spacer arm between the hapten and carrier which may improve the immune response. In order for the compound to be chemically linked to the carrier or bifunctional molecule, it should itself contain a functional group. Preferred functional groups are amino groups, hydroxyl groups and carboxyl groups.

When an animal has been immunized with an immunogenic substance, a wide variety of different antibody-producing cells are stimulated. The antibodies produced by such a response are known as polyclonal antibodies.

Polyclonal antibodies raised against a particular compound do not all bind with the same specificity to that compound. However, it is possible to obtain antibodies which all bind with the same specificity and affinity to a compound. These antibodies are known as monoclonal antibodies.

In order to obtain such monoclonal antibodies, antibody-producing cells are firstly extracted from the spleen of an immunized animal. These cells are then fused with myeloma cells to produce hybridomas. Fusion may be achieved, for example, by treatment with polyethylene glycol. The hybridomas are capable of producing antibodies, like the precursor antibody-producing cells, but are immortal; they are capable of continuous growth in vitro. A number of myeloma cells suitable for fusing with antibody producing cells are known and readily available to those skilled in the art. An example of a suitable myeloma cell which is readily available is PX3-63-AG8-653. This cell is available, for example, from the American Type Culture Collection, Rockville, Maryland, USA under the number ATCC CRL 1580.

Once the antibody-producing cells and the myeloma cells have been fused, the resultant hybridoma cells are separated from the infused cells and cloned by repeated limiting dilution. Cloned hybridomas are then tested to determine which are producing the desired antibodies. This testing may be achieved, for example, by competitive enzyme linked immunosorbent assay (ELISA). Specificity and affinity for a compound may be assessed by the addition of free compound to the ELISA test system to evaluate the ability of the free compound to inhibit binding of the monoclonal antibody to compound which is bound to a solid phase.

Once a particular hybridoma has been selected, monoclonal antibodies may readily be produced in large quantities using well known techniques. If desired, these antibodies may be labelled with an enzyme; e.g. horse radish peroxidase or alkaline phosphatase.

Techniques for producing polyclonal and monoclonal antibodies for a compound are well known to those skilled in the art. Examples of references in which such techniques are described include Methods of Enzymology Volume 70 and Volume 73 Immunochemical Techniques parts A and B respectively Edited by Van Vunakis, H and Langone, J. L., Published by Academic Press 1980 (Part A) and 1981 (Part B), and Kohler, G. and Milstein, C. Nature, Vol. 265, p. 495 (1975).

Marker detection kits

In a further aspect of the invention, a kit is provided for labelling a chemical or chemical composition and/or for identifying the source of a labelled chemical or composition by the above method, said kit comprising at least one inert marker hapten and respective specific binding member or members. Preferably the specific binding member binds the hapten to form an immunological binding pair.

According to a further aspect of this invention we provide an assay kit for detecting the presence of a visually undetectable marker hapten associated with a product, comprising means for providing a sample of said marker in a liquid medium, immunoassay means including antibodies specific for the marker compound, detection means for monitoring the immunoassay and means for comparing the result of the immunoassay with the result expected from a genuine product.

A means for providing a sample of said marker in liquid medium may comprise any solvent necessary for bringing the marker into solution and/or filtration means to remove unwanted solids and/or solid phase extraction columns (for example columns containing an ion exchange resin or a chromatography medium such as silica).

An immunoassay means may employ monoclonal or polyclonal antibodies. The immunoassay means may also include a solid or semi-solid support having sample-receiving areas. Exemplary sample-receiving supports include test tubes, microtiter plates, dipsticks, membranes, lateral flow devices (e.g. immunoassay devices for small molecules (e.g. drugs of addiction) or for pregnancy tests), resins, PVC or latex beads, and nitrocellulose. The sample receiving areas of the support have surface-bound capture reagent hapten capable of binding to a specific binding member (e.g., a hapten specific antibody) or surface bound antibody specific for a marker. Surface-bound hapten may be hapten alone or may be a hapten-protein conjugate or other hapten-polymeric compound which is capable of presenting an epitope of the hapten for binding by a specific binding member. Surface-bound specific binding member may have binding specificity for a hapten used as (or in) the marker (e.g. an antibody specific for an epitope of the hapten) or a specific binding member having specificity for a non-hapten portion of the marker (e.g. an antibody specific for a polymeric compound covalently bound to the hapten).

A detection means for monitoring the result of the immunoassay may be, for example, means to produce and/or measure a detectable reaction. Thus a detection means may comprise an enzyme and a substrate for the enzyme. Preferred detectable labels include enzymes (e.g. horse radish peroxidase, alkaline phosphatase), chemiluminescors (e.g. luciferin), and chromophores (e.g. dyes, colored latex beads, dyed particles, pigments, metal sol particles (e.g. gold or silver metal sol particles), dye encapsulated liposomes, carbon). The detectable label may be attached to the hapten, the anti-hapten antibody, or a second antibody directed against the anti-hapten antibody. Examples of substrates for the detection of the label include o-phenylenediamine dihydrochloride; Amerlite Signal Reagent (available from Amersham International PLC); p-nitrophenol phosphate; and luciferase. It will be appreciated that an external detection device such as a spectrophotometer, luminometer or fluorimeter may be employed. In this way not only the existence of the marker compound but also the amount present can be determined, thus giving an indication of the extent of adulteration of the product.

Another embodiment of the invention features a kit for qualitatively or quantitatively detecting a hapten marker by virtue of a concentration-dependent, physical characteristic of the hapten marker. The kit includes a means for concentrating the hapten marker from a sample of a product. The concentrating means may be provided as a solid support having surface-bound antibody specific for the hapten marker. Binding of hapten from the sample serves to concentrate the hapten, thus facilitating detection of the physical characteristic (e.g. color) of the hapten marker. The solid support may be, for example, a microtiter plate well, a test tube, or an immunoaffinity column. Alternatively, the kit may include a container containing a hapten-specific antibody and a means for concentrating (e.g. immunoprecipitating) antibody-hapten complexes formed by contacting a product sample with the anti-hapten antibody.

The kits described above may also include a means for comparing the result of the detection assay with that expected from a genuine product may comprise instructions describing the result expected of a genuine product (comprising, for example, a colour chart, calibration table or calibration curve), or it may comprise a sample of marked material identical to marked genuine product (to be analyzed alongside the unknown sample).

The kit is preferably provided with a representation of the visually distinctive appearance provided to the material of the genuine product. For example the kit may be provided with a representation of a trademark with which the material of the genuine product is provided.

The ability to provide assay means in kit form ensures that a man in the field, such as a distributor of a product in an environment distant from the product source can quickly check the authenticity of the product without recourse to laboratory facilities.

It will be apparent that, since the marker compound is in such low concentrations in the labelled chemical or composition, its presence therein is not immediately apparent to someone who is unaware of the addition. Furthermore, it would not be easy for a third party to identify the marker using routine techniques and include it in a counterfeit composition. That is because isolation and concentration of the marker relies on the use of an specific binding member specific for the marker and this would not be available to anyone who was ignorant of the identity of the marker.

The invention will now be further described with reference to the following examples.

EXAMPLE 1
Preparation of Protein Conjugates of PBA (m-phenoxybenzoic acid) Intended For Use as a Marker Compound A series of protein conjugates of m-phenoxybenzoic acid (a hapten, referred to hereinafter as 'PBA') were prepared by firstly preparing a suitable reactive derivative from PBA by chemical synthesis followed by conjugation of the derivative with the protein. The derivatives were prepared with a $^{14}C$ radiolabel to allow monitoring of the subsequent protein conjugate to check for removal of reagents and to calculate the loading of the protein with the hapten.

i) Preparation of PBA derivatives m-Phenoxybenzoic acid was reacted with thionyl chloride in benzene to give the corresponding benzoyl chloride which was subsequently reacted with 4-aminobutyric acid in the presence of sodium hydroxide followed by acid hydrolysis to give a derivative a) of the formula below

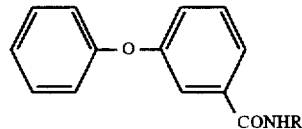

where R is —(CH$_2$)$_3$COOH.

Two further derivatives were prepared by reacting the intermediate benzoyl chloride with b) glycine and c) glycyl glycine in the presence of sodium hydroxide followed by acid hydrolysis to give b) a derivative of formula I where R is —CH$_2$COOH and c) a derivative of formula I where R is —CH$_2$CONHCH$_2$COOH.

The derivative a) of formula I was also prepared by reacting benzyl 4-aminobutyrate and 3-(3'-dimethylaminopropyl)-1-ethyl carbodiimide in aqueous tetrahydrofuran to give a compound of formula I where R is —(CH$_2$)$_3$COOCH$_2$Ph followed by hydrogenolysis with a palladium on charcoal catalyst in tetrahydrofuran to yield derivative a).

The derivatives were converted to their sodium salts (which dissolved readily in water) by addition of stoichiometric amounts of sodium bicarbonate or carbonate in water and tetrahydrofuran added until a homogenous solution was obtained followed by evaporation to dryness.

ii) Preparation of Protein Conjugates

The derivatives prepared as described in i) above, in the form of their sodium salts, were each dissolved in water, adjusted to pH 8 and cooled to 0° C. A solution, also cooled to 0° C. of 3-(3'-dimethylaminopropyl)-1-ethyl carbodiimide was added to the derivative sodium salt and allowed to stand for 2 minutes to complete formation of the isourea carboxylate.

Each of the derivatives was then bonded to one of the following proteins dissolved in distilled, deionized water and filtered:

bovine serum albumin (M.W. about 68,000)
chicken gamma globulin (M.W. 125,000 to 750,000)
keyhole limpet hemocyanin (M.W. 3,000,000 to 7,000,000)

The loading was carried out by adding the solution over one minute to the protein with stirring and the mixture kept at 5° C. for several hours to complete the bonding. pH was adjusted to pH 8 as necessary. The loaded protein was dialyzed with saline phosphate buffer pH 7.3 for from 5 to 7 days with daily changing of dialysate and the loading determined by $^{14}C$ radioactivity measurement.

EXAMPLE 2
Production of Monoclonal Antibodies

A conjugate of PBA and bovine serum albumin (15 moles PBA per mole of protein) was used to produce the antibodies. The PBA-bovine serum albumin was prepared using derivative a) of Example 1 (i) in the procedure of Example 1 (ii).

Six mice (Balb/c, female) were immunized subcutaneously with a 1:1 emulsion of complete Freund's adjuvant and PBA conjugate (0.1 ml, 50 µg). Each animal received a further 3 injections at 3 weekly intervals but with incomplete adjuvant. Under a similar regimen, a further six animals received a higher dose of conjugate (200 μg). Serum samples from the twelve animals were tested for specific binding to PBA by means of an enzyme-linked immunosorbent assay (ELISA).

The spleen was removed from the animal producing the highest serum concentration of antibodies and the splenocytes used in a fusion with PX3-63-AG8-653 myeloma cells (available from the American Type Culture Collection, Rockville, Md., USA, under the number ATCC CRL 1580). Hybridoma cells were distributed into ten 96-well microtiter plates. Following cell growth, supernatant tissue culture fluids were tested by ELISA for antibody production. Specificity was assessed by the addition of free PBA to the test system to determine the inhibition of binding of the antibodies to the solid phase PBA target in the ELISA method. Cells from several positive wells were grown to produce cell stocks and then cloned by the limiting dilution technique. Following further cell growth the resulting supernatants were tested as above and the contents of several positive wells grown-up and cloned again. The cells in wells identified as positive, following the second cloning, were grown-up to produce supernatants containing sufficient monoclonal antibodies for preliminary assay development.

In order to generate sufficient monoclonal antibodies for medium-term requirements, 5 clonal cell hybridomas were chosen for the production of antibody-rich ascites fluid. Ten, pristine-primed, female Balb/c mice per hybridoma, were each inoculated intraperitoneally with up to $10^7$ hybridoma cells. Ascites fluids were harvested, pooled and stored deep frozen.

Antibodies were also prepared by growing hybridoma cells in vitro in stirred tissue culture vessels.

A sample of one of the clonal cell hybridomas has been deposited with the European Collection of Animal Cell Cultures (ECACC), PHLS Centre for Applied Microbiology and Research, Porton Down, Salisbury SP4 OJG, United Kingdom, with effect from 10th January, 1989 under accession number 89011001.

EXAMPLE 3
Assay of a Marked Lubricating Oil

A marked lubricating oil was prepared containing 10 ppm of m-phenoxybenzoic acid. A series of 2 ml samples were prepared containing varying percentages of marked oil and unadulterated oil.

PBA was extracted for assay from each oil sample by the following method.

i) Extraction of PBA from Oil

1. The oil sample on which the authenticity check was to be carried out was placed in a sealable vessel. Five volumes of hexane and 1 volume of 20% acetonitrile in 0.05 M Tris/HCl pH 7.5 were then added to the oil and the vessel sealed. The mixture was then shaken for one minute and the resulting suspension allowed to separate. This took approximately 30 seconds.

2. An aliquot was taken from the lower phase of the separated mixture using a disposable plastics pipette and applied to a 3 ml $NH_2$ Bond Elut column (an ion exchange resin column obtained from Jones Chromatography). The sample of extract was passed through the column by the application of pressure and the column then washed with 4×1 ml aliquots of distilled water.

3. The column was then eluted with 2 ml of a solution of 0.05% (v/v) Tween 20 in saline. This solution removed any bound PBA. Each recovered PBA solution was then subjected to competitive enzyme linked immunosorbent assay (ELISA) by the following method.

ii) Immunoassay Method (with detection by calorimetric means)

1. A plastic well/tube was coated with a fixed level of a PBA-chicken gamma globulin conjugate prepared as described in Example 1. To achieve this coating, a measured aliquot of 100 μl conjugate, at a concentration of 10 μg/ml was placed in the well/tube. This was then incubated at a carefully controlled temperature for a fixed time and a reproducible level of coating was achieved by adsorption. After the coating period, the wells were washed and could be stored at 4° C.

2. The PBA-containing solution to be assayed was placed in a pre-coated well in the presence of a limiting level of specific monoclonal antibody prepared as described in Example 2. The sample of antibody was used at a dilution of 1:1000. The basis of the assay is the competition for binding of this antibody between the PBA in solution and PBA which is immobilized on the surface of the well as conjugate. After a fixed period of time the solution in the well was removed and the well washed. The antibody remaining in the well after washing is that which bound to the immobilized PBA, the level of antibody remaining is thus inversely proportional to the level of PBA which was previously present in free solution.

3. A solution of second antibody-enzyme conjugate was added to the well. The second antibody enzyme conjugate used was IgG (alkaline phosphatase linked to rabbit anti-mouse immunoglobulin G—available from ICN Biologicals) at 1:1000 dilution, 100 μl per well. This conjugate binds to any of the primary antibody which has remained, bound to the immobilized conjugate in the well. The second antibody-enzyme conjugate was added in excess and, again, unbound material was removed by washing. After washing, the level of second-antibody-enzyme conjugate remaining in the well is directly proportional to the level of primary antibody bound in step 2 described above.

4. A solution containing a substrate for the enzyme of the second antibody-enzyme conjugate was added to the well and the level of enzyme present was determined by measuring the formation of colored product. The substrate was p-nitrophenyl phosphate disodium salt (available from Sigma Chemical Co. as Sigma 104 phosphatase substrate) at a concentration of 1 mg/ml in 10% diethanolamine buffer pH 9.8. The formation of yellow colored product was measured at 405 nm using a vertical beam visible light absorption spectrophotometer (MR610 Microplate reader—Dynatech).

Two sets of results of the colorimetric assay of the oil samples containing varying percentages of marked oil are given in Table 2 below. The results are expressed as a percentage of marked oil in the sample.

TABLE 2

| Sample No. | 1 | 2 | 3 | 4 | 5 | 6 | 7 | 8 | 9 | 10 |
|---|---|---|---|---|---|---|---|---|---|---|
| Calculated | 75 | 25 | 100 | 0 | 50 | 0 | 33 | 100 | 10 | 50 |
| Observed Set A | 47 | 14 | 100 | 0 | 50 | 0 | 29 | 100 | 0 | 42 |
| Observed Set B | 76 | 33 | 93 | 0 | 55 | 0 | 22 | 118 | 31 | 55 |

EXAMPLE 4
Assembly of an Assay Kit and its use in an Assay of a Marked Lubricating Oil An assay kit, suitable for testing up to three possible counterfeit samples of lubricating oil, was assembled. The kit comprised:

(1) 5 plastic tubes coated with a PBA-chicken gamma globulin conjugate (prepared as described below);

(2) 5 ion exchange resin columns, (3 ml NH$_2$ Bond Elut columns, obtained from Jones Chromatography);

(3) 5–10 ml volumes of extracting solvent, consisting of 8 ml hexane and 2 ml of 40% acetonitrile in 0.05 M Tris/HCl, pH 7.5;

(4) 1 sample of lubricating oil containing 10 ppm of m-phenoxybenzoic acid (representing a sample of a marked genuine product);

(5) 1 sample of lubricating oil containing no m-phenoxybenzoic acid;

(6) 5–2 ml volumes of PBA-Specific monoclonal antibody diluted ten-fold in phosphate buffered saline (PBS, available in tablet form from Oxoid) containing 0.05% w/v Tween 20 (polyoxyethylene-sorbitan monolaurate, available from Sigma Chemical Company, Catalogue Number P1379);

(7) 1 volume of antibody-enzyme conjugate (comprising horse radish peroxidase conjugated rabbit immunoglobulins to mouse immunoglobulins, available from DAKO Limited, Catalogue Number P161);

(8) Chemiluminescent substrate (Amerlite Signal Reagent, available from Amersham International PLC, Catalogue Number LAN 4400);

(9) Wash solution, consisting of 0.05% (v/v) Tween 20 in saline (ST);

(10) Column wash, consisting of distilled water; and

(11) 1 instruction sheet.

i) Preparation of plastic tubes coated with a PBA-chicken gamma globulin conjugate Plastic tubes were coated with a fixed level of a PBA-chicken gamma globulin conjugate prepared as described in Example 1. To achieve this coating, a measured aliquot of 500 μl conjugate, at a concentration of 20 μg/ml was placed in the tube. This was then incubated for 3 hours at room temperature and a reproducible level of coating was achieved by adsorption. After the coating period, the tubes were washed with the saline/Tween solution (ST), described in Example 3, dried and stored desiccated, preferably at 4° C., until required.

ii) Use of Assay Kit to Assay Marked Lubricating Oils

1. In order to carry out the assay, the first step is to prepare the chemiluminescent substrate, following the manufacturer's instructions.

2. The two samples of lubricating oil belonging to the kit and three "unknown" samples of lubricating oil are extracted using the 5 volumes of extracting solvent and 5 ion exchange columns, according to the method of Example 3. The columns are then washed with two 2 ml aliquots of column wash.

3. Each of the columns is then eluted with one 2 ml aliquot of wash solution into small glass bottles containing the 2 ml volumes of PBA-specific monoclonal antibody.

4. The bottle contents are then mixed, and at least 500 μl from each of the 5 mixtures is transferred to the five plastic tubes coated with PBA-chicken gamma globulin conjugate. After 5 minutes the solutions in the tubes are tipped away and the tubes washed once with wash solution.

5. 500 μl of a solution of the antibody-enzyme conjugate is added to each of the tubes. After a 5 minute incubation the contents of the tubes are tipped away and the tubes are washed 5 times with wash solution.

6. The chemiluminescent substrate, 1 ml, is then added to the tube and after 2 minutes the light output measured, following the manufacturers instructions for use of a portable, battery powered, tube liminometer (available from Dynatech Laboratories Ltd.). The read-out of the instrument is a 3 digit number in the range 0–999.

7. The reproducibility of the method has been assessed over a series of 35 assays, carried out by two operators, over a four week period. The inter-assay coefficient of variation (CV) for this series of experiments was 9.1%. It was found that if the assay had been performed correctly, the ratio of the positive control (lower reading) to the negative control (higher reading) was 0.612±0.056 (i.e.±1 Standard Deviation (SD). For an "unknown" oil a value of 0.725 or greater indicated a "possible counterfeit" sample.

EXAMPLE 5

Assay of marked gasoline 13 ml samples of leaded and unleaded gasoline were marked with 3 levels of PBA (10, 5 and 2.5 ppm). They were extracted with Tris buffer (2 ml, 0.05 M, pH 7.5). The extracts were assayed as described in Example 3 and PBA quantified using a calibration curve of standards prepared in an unmarked gasoline extract. Corresponding samples were prepared containing radiolabelled PBA enabling extraction efficiencies to be determined and allowing comparison between observed and expected values. The results are shown in Table 3.

TABLE 3

A comparison of observed and expected values for aqueous extracts assayed against a calibration curve in unmarked gasoline extract

| Sample | Blank | 10 ppm Extract | 10 ppm Extract diluted | | | 5 ppm Extract | 5 ppm Extract diluted | | 2.5 ppm Extract |
|---|---|---|---|---|---|---|---|---|---|
| | | | 1:2 | 1:4 | 1:8 | | 1:2 | 1:4 | |
| Leaded gasoline | | | | | | | | | |
| Expected (radiochemistry) | 0 | 46* | 23 | 11.5 | 5.7 | 23 | 11.4 | 5.7 | 11.4 |
| Observed | 0.9 | 47 | 22.5 | 11.0 | 6.4 | 29 | 13.5 | 5.3 | 13.5 |
| Unleaded gasoline | | | | | | | | | |
| Expected (radiochemistry) | 0 | 33 | 16.2 | 8.1 | 4.1 | 15.5 | 7.7 | 3.9 | 7.5 |
| Observed | 0.9 | 41 | 18.5 | 7.0 | 3.8 | 14.5 | 6.2 | 3.4 | 7.6 |

*All values quoted in ppm.

TABLE 3-continued

A comparison of observed and expected values for aqueous extracts assayed against a calibration curve in unmarked gasoline extract

| Sample | 10 ppm Blank | 10 ppm Extract | 10 ppm Extract diluted 1:2 | 1:4 | 1:8 | 5 ppm Extract | 5 ppm Extract diluted 1:2 | 1:4 | 2.5 ppm Extract |
|---|---|---|---|---|---|---|---|---|---|

These results demonstrate the concentration effect achieved by extracting PBA from 13 ml of gasoline into 2 ml of Tris buffer, and convincingly demonstrate that gasoline marked with PBA may be distinguished from unmarked gasoline by immunoassay.

EXAMPLE 6
Assay of marked pharmaceutical

Marked Samples of Paracetamol (acetaminophen—a mild pain killer and anti-pyretic agent) and Naproxen (a non-steroidal anti-inflammatory agent) were prepared containing 20 ppm solid PBA. Portions of each (1 g) were added to 10 ml of PBS/Tween (described in Example 4) in a 20 ml glass bottle. Similarly non-marked assay blanks were prepared for both materials. The bottles were tumbled overnight to extract the PBA into the PBS/Tween. Following separation of undissolved material by centrifugation, sample aliquots (250 μl) of the supernatant solutions were added to 250 μl of PBA specific antibody and analyzed using an assay kit, similar to that described in Example 4.

From the results presented in Table 4 it was demonstrated that the marked pharmaceuticals were clearly distinguishable from the non-marked pharmaceuticals.

TABLE 4

| Drug | Unmarked* | Marked* | Ratio (%) |
|---|---|---|---|
| Paracetamol | 400 | 288 | 72 |
|  | 394 | 275 | 70 |
|  | 377 | 283 | 75 |
|  | 378 | 278 | 74 |
|  | 281 | 206 | 73 |
|  | 266 | 203 | 76 |
|  | 386 | 303 | 78 |
|  | 398 | 267 | 67 |
|  | 517 | 357 | 69 |
|  | 480 | 378 | 79 |
|  | 469 | 379 | 80 |
|  | Mean Ratio-74 | S.D. = 4.2 | C.V. = 5.7% |
| Naproxen | 517 | 350 | 68 |
|  | 503 | 337 | 67 |
|  | 355 | 260 | 73 |
|  | 313 | 226 | 72 |
|  | 279 | 185 | 66 |
|  | 269 | 220 | 81 |
|  | 269 | 204 | 76 |
|  | 245 | 153 | 64 |
|  | Mean Ratio = 71 | S.D. = 5.7 | C.V = 8.0% |

*Values indicated were read from the tube liminometer described in Example 4.

*Values indicated were read from the tube liminometer described in Example 4.

It is likely that the nature of extraction solvents and eluent solvents would be dependent on the nature of the chemicals chosen for spiking individual substrates. However, the results described here show that it is possible to add low concentrations of small organic molecules to pharmaceutical products and to use immunoaffinity chromatography to identify and distinguish between batches of the product.

EXAMPLE 7
Assay of marked perfume

A sample of 'Eau de Cologne' was prepared containing 20 ppm of PBA. 2 ml of this marked material and 2 ml of the unmarked material were placed in small glass test tubes and evaporated in a gentle air stream to incipient dryness. 2 ml of PBS/Tween (described in Example 4) was added to the oily residue and the tube contents mixed vigorously by vortex mixing. The insoluble, heavier than water, oil was then separated by centrifugation and sample aliquots of the supernatant solution were analyzed as described in Example 6. From the results presented in Table 5 it was demonstrated that the marked perfume was clearly distinguishable from the unmarked equivalent.

TABLE 5

| Perfume | Unmarked* | Marked* | Ratio (%) |
|---|---|---|---|
| Eau de Cologne | 866 | 104 | 12 |
|  | 851 | 243 | 29 |
|  | 655 | 107 | 16 |
|  | 722 | 133 | 18 |
|  | 710 | 126 | 18 |
|  | 782 | 196 | 25 |
|  | Mean Ratio = 20 | S.D. = 6.2 | C.V. = 31.6% |

*Values indicated were read from the tube liminometer described in Example 4.

*Values indicated were read from the tube liminometer described in Example 4.

As an alternative approach marked and unmarked Eau de Cologne were diluted ten-fold with PBS/Tween and assayed directly as outlined in Example 6. The results are presented in Table 6 and show that this alternative method also permits clear distinction between unmarked and marked perfume.

TABLE 6

| Perfume | Unmarked* | Marked* | Ratio (%) |
|---|---|---|---|
| Eau de Cologne | 736 | 499 | 68 |
|  | 760 | 522 | 69 |
|  | 494 | 324 | 66 |
|  | 382 | 267 | 70 |
|  | 401 | 233 | 58 |
|  | 385 | 257 | 68 |
|  | 352 | 210 | 60 |
|  | 484 | 307 | 63 |
|  | 640 | 426 | 67 |
|  | Mean Ratio = 65.4 | S.D. = 4.2 | C.V.-6.4% |

EXAMPLE 8
Assay of marked drink

A sample of blended whisky was prepared containing 20 ppm of PBA. The marked whisky and a corresponding sample of the unmarked whisky were diluted 4-fold with PBS/Tween and sample aliquots (250 μl) were analyzed using the method described in Example 6. The results presented in Table 7 demonstrate that the marked whisky is clearly distinguishable from the unmarked whisky.

TABLE 7

| Drink | Unmarked* | Marked* | Ratio (%) |
| --- | --- | --- | --- |
| Whisky | 375 | 119 | 31 |
| | 396 | 158 | 39 |
| | 381 | 180 | 47 |
| | 449 | 110 | 25 |
| | 435 | 104 | 24 |
| | 427 | 109 | 26 |
| | 431 | 95 | 22 |
| | 421 | 116 | 28 |
| | 387 | 117 | 30 |
| | 440 | 86 | 19 |
| | 412 | 122 | 30 |
| | 386 | 122 | 32 |
| | 353 | 107 | 30 |
| | 474 | 115 | 24 |
| | 452 | 106 | 23 |
| | 446 | 111 | 25 |
| | Mean Ratio = 28.4 | S.D. = 6.9 | C.V. = 24% |

*Values indicated were obtained from the tube liminometer described in Example 4. It was noted in this Example that the signal generated took approximately 20 minutes to develop.

EXAMPLE 9
Covert Surface Marking

In one application of the invention, it is desired to apply the hapten molecule to a surface using an impact or non-impact printing method. The laid down hapten can be subsequently visualized by the application of the other member of the specific binding pair. Since haptens are either not compatible with the ink formulation or do not have good adhesion properties to the surface, it is sometimes necessary to bond the hapten to a polymeric backbone. The hapten-polymer is soluble in the ink formulation and can still be recognized by the specific binding pair member when applied. It should show good adhesive properties to surfaces such as glass, plastic or metal.

In one embodiment of the method, the hapten is chemically linked to a polymer through suitable conjugation chemistry. The subsequent hapten-reacted polymer is dissolved or suspended in an ink formulation capable of being applied through ink jet printing, array jet printing, flexographic printing, lithographic printing, screen printing, hand stamping, or any conventional printing. Once dry, the hapten-polymer can be revealed by application of the specific binding pair linked to a signal compound such as an enzyme, latex bead or fluorescent tag.

The hapten polymer conjugates can be used not only to label surfaces, but can be incorporated into products (either liquids or solids) as well.

Below is given a specific example of hapten-polymer conjugation.

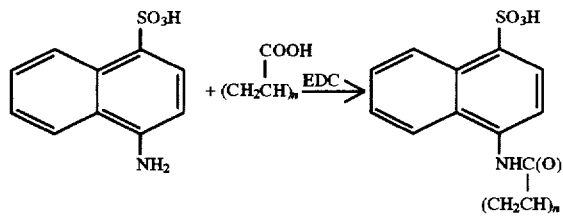

1-Amino-4-naphthalene-sulphonic acid (ANS) (220 mg) and polyacrylic acid (1.4 g) are dissolved in HPLC grade water (25 ml). Dimethylaminopropyl-ethylcarbodiimide) (300 mg) is added in 50 mg portions over 1 hour, adjusting the pH to 5.5 (with 1 M hydrochloric acid) after each addition. The solution is subsequently stirred overnight at room temperature. Following this, the reaction mixture is dialyzed against HPLC grade water (five times against 5 liters each time) over a period of five days. The resulting dialysate is freeze-dried for storage.

EXAMPLE 10
Preparation of immunoaffinity columns for hapten marker detection An immunoaffinity resin is prepared by reacting cyanogen bromide Sepharose CL-4B resin (Pharmacia Ltd) with a hapten-specific monoclonal antibody (ratio 1 ml resin to 2.5 mg of antibody). Cyanogen bromide Sepharose CL-4B is activated by swelling in 75 ml/g of 1 mM HCl. The resin is then washed with 5 ml/g of coupling buffer (100 mM sodium hydrogen carbonate, 500 mM sodium chloride, pH 8.3). The antibody is diluted to 1.56 mg/ml with PBS followed by diluting with an equal volume of coupling buffer. This mixture is reacted with the swelled, washed resin for 1 hour at room temperature with mixing. The resin is filtered and mixed with ethanolamine (1 M at pH 8.0) for 1 hour at room temperature. The resin is washed and stored with PBS containing 0.05% w/v sodium azide at pH 7.4. Aliquots of the finished resin (0.04 ml settled bed volume) are supported between porous frits in plastic columns. These columns are examined for their ability to bind control samples containing known amounts of a hapten marker. The control samples are applied in 50 ml of PBS and eluted with acetonitrile (2 ml). Quantification of the hapten marker retained by the column is accomplished by HPLC analysis.

EXAMPLE 11
Preparation of [4-amino-1,1-azobenzene-3,4-disulphonic acid]-protein conjugates The following solutions were prepared and cooled to 0° C.:1) chicken gamma globulin (CGG) (72 mg) dissolved in PBS (20 ml); 2) a filtered solution of the color-coded antigen 4-amino-1,1-azobenzene-3,4-disulphonic acid (Butterfield Laboratories, King's Lynn, Norfolk) (144 mg) in 1 M HCl (10.0 ml); and 3) a NO₂ solution (10%, 50 ml). The three solutions were mixed under rapid stirring at 0° C. After 10 min. the solution was dialyzed against distilled water (5×5 l) for about five days. The supernatant was lyophilized and the product was stored at −20° C.

EXAMPLE 12
Preparation of [4-amino-1,1-azobenzene-3,4-disulphonic acid]-DMG-BSA used for screening.

A DMG-BSA conjugate was prepared by adding 3,3-dimethyl glutaric anhydride (DMG) (1.0 g) to a rapidly stirring solution of bovine serum albumin (BSA) (1.0 g) in phosphate-buffered saline (PBS) (50 ml). The pH of the solution was monitored and continually re-adjusted to pH 7–8 by addition of 1 M sodium hydroxide. After the first half hour of stirring, the pH was checked every 30 minutes. The pH change was less than 0.2. The reaction mixture was stirred overnight at room temperature. The pH was checked again and adjusted if needed. The sample was dialyzed against distilled water (5×5 l) for about five days, lyophilized, and stored at −20° C.

4-amino-1,1-azobenzene-3,4-disulphonic acid (75 mg) was added to a mixture of 1-ethyl-3-(3-dimethyl aminopropyl carbodiimide) (EDC) (81 mg) and DMG-BSA (80 mg) in PBS (10.0 ml). The reaction mixture was stirred overnight at room temperature. The sample was dialyzed against distilled water (5×5 l) for about five days, lyophilized, and stored at −20° C. The conjugate of 4-amino-1,1-azobenzene-3,4-disulphonic acid to DMG-BSA was shown to have an incorporation ratio of 40.

EXAMPLE 13
Immunization of mice with the [4-amino-1,1-azobenzene-3,4-disulphonic acid]-CGG conjugate and antibody screening The freeze-dried |4-amino-1,1-azobenzene-3,4-disulphonic acid|-CGG conjugate was dissolved to 2 mg/ml in phosphate buffered saline pH 7.4 (PBS), then mixed with an equal volume of Freund's adjuvant. The mixture was thoroughly homogenized to form a stable suspension and either immediately used for immunization or stored at 2° to 8° C. before use. Ten mice were each immunized by intraperitoneal injection of up to 300 µl of the |4-amino-1,1-azobenzene-3,4-disulphonic acid|-CGG suspension, which contained up to 300 µg of the conjugate. Two to three weeks after the first immunization the mice were immunized a second time. A serum sample was taken from each mouse two weeks after the second immunization.

Serum samples were analyzed by titration ELISA to determine the amount of circulating antibody in the mouse, and hence the magnitude of the immunological response to the conjugate. ELISA plates were coated with a 1 µg/ml solution of |4-amino-1,1-azobenzene-3,4-disulphonic acid|-BSA conjugate solubilized in PBS solution to a concentration of 1 µg/ml. A 50 µl portion of the conjugate was used to coat each well of a 96-well plate to provide 50 ng of conjugate per well. A series of diluted serum samples were applied to the |4-amino-1,1-azobenzene-3,4-disulphonic acid|-BSA coated plates. Bound serum antibodies were detected by binding peroxidase-labeled, rabbit anti-mouse antibody. Binding of the peroxidase-labeled antibodies was visualized by the addition of the tetramethyl benzidine (TMB) substrate. The reaction was stopped by the addition of 20% v/v sulphuric acid. The maximum dilution of the serum sample that gave an absorbance value of at least 0.2 absorbance units at a wavelength of 450 nm in the ELISA was recorded.

In order to assess the affinity of the circulating antibodies, suboptimal dilutions of the sera (as determined by titration ELISA) were analyzed in a competitive ELISA using varying concentrations of 4-amino-1,1-azobenzene-3,4-disulphonic acid. Prior to application to the ELISA plates, 4-amino-1,1-azobenzene-3,4-disulphonic acid was solubilized to a concentration of 1 mg/ml using PBS, then diluted to a series of microgram concentrations using PBS containing 1% w/v BSA. The concentration of the 4-amino-1,1-azobenzene-3,4-disulphonic acid required to reduce binding of serum antibody in the ELISA by 50% was determined ($IC_{50}$) for each sample.

The results of the analyses described above were then used to select a mouse for fusion and hybridoma production. A mouse considered suitable for fusion was required to have a maximum titration of at least 1/10,000 and an $IC_{50}$ of 3 µg/ml or less. The serum from the mouse selected for fusion had a maximum titer of 1/20,000 and an $IC_{50}$ of 1.3 µg/ml.

The immune response of the selected mouse was primed by intravenous inoculation of approximately 100 µl of a 1 mg/ml solution of the |4-amino-1,1-azobenzene-3,4-disulphonic acid|-CGG conjugate. This was filter sterilized using a 0.2 µm filter prior to inoculation. The fusion was performed three days after intravenous inoculation. The cells isolated from the spleen were fused with the P3X63Ag8.6.5.3 myeloma cell line at a ratio of 20:1. The fusion product was cultured in HAT medium containing 20% v/v FCS, which allows selective growth of hybridoma cells. The fusion mixture was distributed across twenty×24-well tissue culture plates (480 individual 2 ml cultures). A sample of unfused cells served as a negative control. The cultures were maintained at 37° C., 5% v/v $CO_2$, in a humidified incubator until clones of hybridoma cells were visible.

Samples of the growth medium were taken from each of the 2 ml cultures (480 in total) and tested in a competitive ELISA for the presence of antibody with an affinity for 4-amino-1,1-azobenzene-3,4-disulphonic acid. 4-amino-1,1-azobenzene-3,4-disulphonic acid was solubilized to a concentration of 1 mg/ml in PBS, and diluted to concentrations ranging from 10 µg/ml to 1 µg/ml using PBS containing 1% w/v ovalbumin. Each fusion culture was analyzed by placing an undiluted sample in a well of the |4-amino-1,1-azobenzene-3,4-disulphonic acid|-BSA coated ELISA plate in either the presence and absence of 4-amino-1,1-azobenzene-3,4-disulphonic acid solution. The concentrations of 4-amino-1,1-azobenzene-3,4-disulphonic acid used were 1 and 10 µg/ml.

In the present example, $4.3 \times 10^8$ splenocytes were fused with $2.15 \times 10^7$ myeloma cells to produce an average of 6.46 hybridoma clones in each of the 480 culture wells. A total of 35 fusion cultures were selected using 4-amino-1,1-azobenzene-3,4 -disulphonic acid in the competitive ELISA screen. Cells selected for further development were those associated with growth medium samples which gave absorbance readings greater than 1.0 in the ELISA screen in the absence of 4-amino-1,1-azobenzene-3,4-disulphonic acid, and inhibited by more than 90% by 0.1 mg/ml of 4-amino-1,1-azobenzene-3,4 -disulphonic acid in the competitive assay.

Cells from 19 of the fusion cultures were re-suspended and cloned by limiting dilution. Cell suspensions were adjusted to six viable cells per ml and distributed across one 96-well culture plate, 100 µl per well, containing a feeder cell layer. Once the clones were visible, supernatant samples from each of the 96 wells were assessed by ELISA for the presence of antibody capable of binding the |4-amino-1,1-azobenzene-3,4-disulphonic acid|-CGG conjugate. Wells containing a single clone that produced an anti-|4-amino-1,1-azobenzene-3,4-disulphonic acid| antibody were selected as monoclonal cell lines. These cell lines were gradually expanded in culture through a series of culture vessels which contained a splenocyte feeder layer. After the clones were expanded to a 10 ml culture flask, the hybridomas were weaned off the splenocyte feeder layer.

Nineteen monoclonal cell lines were isolated that produced antibody that binds to the |4-amino-1,1-azobenzene-3,4 -disulphonic acid|-BSA conjugate in the ELISA. These were successfully expanded into stable cell cultures.

During expansion of the cell cultures, media samples from the cultures were monitored for antibody production. These samples were analyzed by titration ELISA as described above. Culture media samples were analyzed as a series of five-fold dilutions, and the maximum dilution that still gave significant color in the ELISA (maximum titre) was determined. In addition, the affinity of the antibodies produced by the cell lines was determined by competitive ELISA. A suboptimal dilution of the antibody was selected from the titration ELISA and applied to the ELISA plate in the presence of different concentrations of 4-amino-1,1-azobenzene-3,4 -disulphonic acid. The concentration of 4-amino-1,1-azobenzene-3,4-disulphonic acid that reduced antibody binding by 50% in the ELISA was determined ($IC_{50}$).

The cell line 4A2E12 was selected for further work on the basis of antibody productivity in culture and the affinity of the antibody to 4-amino-1,1-azobenzene-3,4-disulphonic acid. Culture supernatant from the 4A2E12 cell line contained antibody with a maximum titer of 1/3125 and an $IC_{50}$ of 9 ng/ml.

A master cell bank (MCB) was produced from which working cell banks (WCBS) are created. Working cell banks serve as a readily available source of cells for antibody production. Aliquots of the 4A2E12 cell line were prepared for long-term storage. The cells were expanded in HT +10% v/v FCS medium, pelleted by centrifugation, and resuspended in freezing medium. The suspension was aliquotted into 12 cryovials, each containing at least $5 \times 10^8$ viable cells (determined by the exclusion of a vital dye). The vials were sealed, insulated and stored at approximately −70° C. for seven days. Vials were then immersed in liquid nitrogen for long term storage.

A single vial was retrieved from the MCB and the cells expanded in culture and used to prepare a WCB using a similar method to that described for the MCB. Supernatant retained from the culture was used to set up the WCB for analysis of antibody content by ELISA.

A single vial of cells was retrieved from the WCB for evaluation. A sample was taken directly from the thawed vial and incubated in tryptose broth for assessment of sterility. The remaining cell suspension was expanded in antibiotic free medium. Two days after retrieval, cell viability was assessed by exclusion of a vital dye. A sample of the cell culture was sent to the European Collection of Animal Cell Cultures, Porton Down for analysis of Mycoplasma contamination. Cells retrieved from the WCB were maintained in culture for approximately 120 days. During this time, the monoclonality of the cells, antibody productivity by application of culture supernatant to ELISA), and the division rate of the cells were monitored.

The monoclonality of the 4A2E12 cell line was determined by repeating the limiting dilution procedure described above. The cells were diluted to a concentration of six viable cells per ml and placed in five 96-well tissue culture plates containing a layer of splenocyte feeder cells. After approximately two weeks, the position of clones on the culture plates was recorded. Samples of culture media were taken from each well and applied to ELISA plates coated with the [4-amino-1,1-azobenzene-3,4-disulphonic acid]-BSA conjugate. The percentage correlation of the position of the clones and wells containing antibody was determined.

The maximum concentration of antibody in culture supernatants of the 4A2E12 cell line was 30 µg/ml as determined by ELISA. Two days after retrieval from liquid nitrogen the cells were 94.3% viable. The monoclonality of the cell line was assessed at 98% with an accuracy of ±9.96%.

EXAMPLE 14
Bulk Production and Purification of the 4A2E12 Antibody

The 4A2E12 cell line was weaned from HT medium containing 20% v/v FCS into HT medium +5% v/v Nuserum medium. The cultures were expanded up to a volume of approximately 200 ml in large culture flasks in medium supplemented with 5% v/v Nuserum. The cultures were grown either in a Techne-stirred and roller culture (both using the batchfill principle) or in an orbital shaker culture (batch culture). These two culture systems were established by the transfer of the cell suspensions from the three 200 ml flask cultures prepared above. The antibody productivity of these cultures was determined by HPLC using a protein A affinity column. The antibody-containing medium was harvested from the different culture vessels, pooled, clarified by filtration (0.2 µm), and concentrated by ultrafiltration using a molecular weight cut-off of 20 kDa. The antibody was then purified from the concentrate by ammonium sulphate precipitation. The concentration of antibody (determined by protein A HPLC) in each of the three culture systems ranged from 10 µg/ml to 1.5 mg/ml. Such levels of antibody productivity in the culture systems used are considered to be highly satisfactory.

EXAMPLE 15
Preparation of Tagged Polymers: Synthesis of Polyallylamines Tagged with Mordant Yellow 7

1-ethyl-3-(3-dimethyl aminopropyl carbodiimide) (EDC) (5.0 g) was added to a solution of polyallylamine (10.0 g) in distilled water (100 ml). A suspension of Mordant Yellow 7 (20 g) in distilled water (50 ml) was added under vigorous stirring. After stirring for 30 min. at room temperature, an additional portion of EDC (5.0 g) was added and the mixture was left stirring overnight. The remaining solid was removed by centrifugation (20 min., 2000 rpm). The supernatant was dialyzed against distilled water (5×5 liters) for about five days. The sample was then removed from the dialysis tubing and the liquid was removed under reduced pressure using a rotary evaporator. A total of 5 g of hapten-labeled polymer was produced by this method.

EXAMPLE 16
Synthesis of Phenolic Resin Polymer Tagged with Mordant Yellow 7

The following solutions were prepared: 1) a 75 mg/ml solution of triethylamine (1030 µl) and tetrahydrofuran (THF) (8970 µl); 2) a 100 mg/ml solution of isobutylchloroformate (950 µl) and THF (9050 µl); and 3) a solution of Mordant Yellow 7 (1.3 g) suspended in THF (100 ml). The solutions were cooled (−5° C.) using a salt ice bath. The triethylamine (6250 µl) and isobutylchloroformate solution (6250 µl) were added to the Mordant Yellow 7 suspension under stirring. Stirring was continued for 25 min. at −5° C. A solution of phenolic resin (10.0 g) dissolved in 33% pyridine/distilled water (90 ml) was added to the mixture. The reaction mixture was kept at 4–6° C. for 30 min., allowed to warm to room temperature, and stirred overnight. The sample was dialyzed against distilled water (5×10 l) for five days, from the dialysis tubing, and dried under reduced pressure using a rotary evaporator. This method yielded about 13 g of hapten-labeled polymer.

EXAMPLE 17
Formulation of a Tagged Polymer into a Suitable Ink for Cover Surface Marking The composition of a typical ink for inkjet printing purposes containing tagged polymer is as follows:

| | |
|---|---|
| Methylethyl ketone or ethanol | 31% v/v |
| Acetone | 50% v/v |
| Binder such as phenolic resin | 17% w/v |
| Sodium chloride | 2% w/v |

A tagged polymer is admixed in the above composition at a suitable concentration and printed onto a surface using an inkjet printer. The conductivity of an ink formulation for inkjet printing preferably has a conductivity of 1100 micro-Sieverts and a viscosity of 4 centipoise.

Other inks that the polymer can be admixed with include flexographic or lithographic inks, gravure inks, intaglio inks or any other surface coating including paints, polymer films, etc.

EXAMPLE 18
Admixing of the Hapten-Polymer Marker into a Product

The tagged polymer prepared as described above in Examples 15 or 16 is admixed with a polymer preparation such as PVC chips or nylon granules. The polymer is melted and extruded into a form such as a door or window frame or a textile. The hapten-polymer marker incorporated into the extruded material can be detected by dipping the marked item (or a fraction of the item) into a solution containing a specific binding member.

EXAMPLE 19
Detection of a Marker in a Marked Product by Binding of a Specific Binding Member The following solutions are used in the detection of a hapten-polymer marker, where the hapten is 4-amino-1,1-azobenzene-3,4-disulphonic acid:
1. 0.5% Tween/PBS.
2. 4-amino-1,1-azobenzene-3,4-disulphonic acid antibody (the neat sample (18.4 mg/ml) may be diluted 10 fold using 0.5% Tween/PBS).

3. Rabbit anti-mouse antibody conjugated to peroxidase (diluted 10 fold using 0.5% Tween/PBS).

4. Developer solution for detection of the peroxidase label (TMB substrate kit (Vector Laboratories; Cat no. SK-4400).

The following steps are performed to detect the [4-amino-1,1-azobenzene-3,4-disulphonic acid]-polymer marker:

1. Wash the sample in 0.5% Tween/PBS.
2. Incubate the sample in the anti-[4-amino-1,1-azobenzene-3,4-disulphonic acid] antibody solution for 5 min.
3. Wash the sample again in 0.5% Tween/PBS.
4. Incubate the sample in the peroxidase labeled, rabbit anti-mouse antibody solution for 5 min.
5. Wash the sample in 0.5% Tween/PBS.
6. Develop the sample with the developer solution for up to 5 min.

EXAMPLE 20
Preparation of a Hapten-Labeled Functional Monomer

A hapten-labeled functional monomer is prepared by reacting glycidyl methacrylate with 4-amino-1-naphthalenesulfonic acid. This synthesis is conducted by dissolving 22.3 grams 4-amino-1-naphthalenesulfonic acid in 100 grams methylene chloride and slowly adding 14.2 grams glycidyl methacrylate with stirring. After reacting to completion, the hapten-labeled monomer product is recovered by vacuum stripping to remove the volatile solvent.

EXAMPLE 21
Preparation of a Hapten-Labeled Polymer Marker by Polymerization of a Hapten-Labeled Functional Monomer The hapten-labeled functional monomer from the previous paragraph is copolymerized with a unlabeled monomer to produce a hapten-labeled polymer. For example, after dissolving 100 grams of the monomer adduct described in Example 20 and 100 grams methyl methacrylate in 800 grams of acetone, the solution is heated to reflux. Then, one gram of benzoyl peroxide is added to the comonomer solution. Polymerization is allowed to proceed to completion (6–12 hours). After cooling, the copolymer is recovered by adding sufficient water to precipitate the product, followed by filtration, washing and drying.

EXAMPLE 22
Preparation of a Hapten-Polymer by Derivitization of a Pre-Formed Polymeric Compound An un-labeled copolymer is first prepared and then derivatized by reaction with a suitable hapten. For example, a solution copolymer is prepared by copolymerizing 100 grams methyl methacrylate and 100 grams glycidyl methacrylate in 800 grams acetone, as described above. Then, 4-amino-1-naphthalenesulfonic acid is added to the copolymer solution to form a hapten-labeled polymer.

EXAMPLE 23
Detection of a Hapten Marker by Detection of a Physical Characteristic of the Hapten A sample of gasoline is assayed for the presence of a Mordant Yellow 7-polymer marker by first extracting with solvent and aqueous buffer. A sample of gasoline having a known amount of the Mordant Yellow 7-polymer marker is used as a control. The extracts are applied to an immunoaffinity column containing bound anti-Mordant Yellow 7 antibody. The column is then washed 4 times with distilled water. The bound Mordant Yellow 7-polymer marker is eluted from the column with a solution of 0.05% (v/v) Tween 20 in saline. The sample is then evaporated and the presence of the Mordant Yellow 7-polymer marker determined by comparison to the control sample. Where the sample contains the Mordant Yellow 7-polymer marker, the evaporated sample appears colored. Where desired, the intensity of the color is analyzed by spectrophotometry to determine the amount of Mordant Yellow 7-polymer marker present in the product.

EXAMPLE 24
Detection of a Hapten Marker by Detection of a Physical Characteristic of the Hapten A sample of gasoline to be tested for the presence of the Mordant Yellow 7-polymer marker is extracted and passed through an immunoaffinity column as described above. The sample fraction which bound to the column is then eluted. The presence of the Mordant Yellow 7-polymer marker is then detected by immunoassay. The samples are placed in a tube which has surface-bound anti-Mordant Yellow 7 antibody, incubated for 5 min at room temperature, and then washed with 0.5% Tween/PBS. The color of the test sample (as a result of the binding of Mordant Yellow 7-polymer to the assay tube) is compared to that of the control samples to determine the presence of the Mordant Yellow 7-polymer marker. The amount of Mordant Yellow 7-polymer marker present in the sample is determined by spectrophometric analysis.

REFERENCE LIST

Voller A., Bidwell D. E., Bartlett A. (1979). The Enzyme Linked Immunosorbent Assay (ELISA). A Guide With Abstracts of Microplate Applications Available From Dynatech Europe, Borough Hosue, Rue du Pre, Guernsey.

Other embodiments are within the scope of the following claims.

What is claimed is:

1. A method of monitoring or tracing a process chemical or specialty additive, said method comprising:
   (a) associating said chemical or said additive with a marker, said marker comprising a hapten covalently bound to a pre-formed polymeric compound, said marker being not already associated with said chemical or additive;
   (b) obtaining a sample from the process or product in which said chemical or additive is employed; and
   (c) measuring the concentration of the marker in said sample by subjecting said sample to an immunoassay specific for said marker.

2. The method of claim 1, wherein said process chemical or specialty additive is selected from the group consisting of biocides, water treatment chemicals, food additives, plastics additives, and petroleum product additives.

* * * * *

UNITED STATES PATENT AND TRADEMARK OFFICE
CERTIFICATE OF CORRECTION

PATENT NO. : 5,776,713
DATED : July 7, 1998
INVENTORS : Ronald Colin Garner, David J. Phillips, Timothy G. Wilkinson, Frank G. Angella, Erwin R. Dorland, and Martin W. Stow It is certified that error appears in the above-identified patent and that said Letters Patent is hereby corrected as shown below:

On the title page, item [56],
Under "References Cited, Other Publications", please add the following reference:

Voller et al., *Manual of Clinical Laboratory Immunology*, Editors: Rose et al., Published 1986, pp. 99-109

Signed and Sealed this

Sixteenth Day of February, 1999

Attest:

*Acting Commissioner of Patents and Trademarks*

Attesting Officer